US010526371B2

(12) United States Patent
Hoogenboom et al.

(10) Patent No.: US 10,526,371 B2
(45) Date of Patent: Jan. 7, 2020

(54) HYDROGEL-FORMING PEPTIDES

(71) Applicants: Universiteit Gent, Ghent (BE); Vrije Universiteit Brussel, Brussels (BE)

(72) Inventors: Richard Hoogenboom, Terneuzen (NL); Annemieke Madder, Massemen (BE); Steven Ballet, Itegem (BE)

(73) Assignees: Universiteit Gent, Ghent (BE); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 15/743,357

(22) PCT Filed: Jul. 13, 2016

(86) PCT No.: PCT/EP2016/066583
§ 371 (c)(1),
(2) Date: Jan. 10, 2018

(87) PCT Pub. No.: WO2017/009358
PCT Pub. Date: Jan. 19, 2017

(65) Prior Publication Data
US 2018/0201648 A1 Jul. 19, 2018

(30) Foreign Application Priority Data

Jul. 13, 2015 (EP) ..................................... 15176415

(51) Int. Cl.
*A61K 47/42* (2017.01)
*C07K 7/02* (2006.01)
*C07K 7/06* (2006.01)
*A61K 31/496* (2006.01)

(52) U.S. Cl.
CPC .............. *C07K 7/06* (2013.01); *A61K 31/496* (2013.01); *A61K 47/42* (2013.01); *C07K 7/02* (2013.01)

(58) Field of Classification Search
CPC ...... A61K 38/08; A61K 38/10; A61K 47/183; A61K 47/42; C07K 7/02
See application file for complete search history.

(56) References Cited

U.S. PATENT DOCUMENTS

| 3,891,616 A * | 6/1975 | Ondetti ................ C07D 207/08 530/328 |
| 2005/0181973 A1 | 8/2005 | Genove et al. |
| 2014/0302144 A1 | 10/2014 | Koutsopoulos et al. |

FOREIGN PATENT DOCUMENTS

| EP | 0498508 A1 | 8/1992 |
| EP | 2180027 A1 | 4/2010 |
| GB | 2496654 A | 5/2013 |
| JP | 2012082180 A | 4/2012 |
| WO | 2013072686 A2 | 5/2013 |
| WO | 2014152751 A1 | 9/2014 |
| WO | 2015116242 A1 | 8/2015 |
| WO | 2017009358 A1 | 1/2017 |
| WO | WO-2017140792 A1 * | 8/2017 ......... A61K 49/0073 |

OTHER PUBLICATIONS

Hariton et al. Bioavailability of beta-amino acid and C-terminally derived PK/PBAN analogs. Peptides. May 22, 2009, vol. 30, pp. 2174-2181. (Year: 2009).*
Mangelschots et al. Mixes alpha/beta-Peptides as a Class of Short Amphipathic Peptide Hydrogelators with Enhanced Proteolytic Stability. BioMacromolecules. Jan. 7, 2016, vol. 17, pp. 437-445. (Year: 2016).*
Bibian et al., Rational design of hexapeptide hydrogelator for controlled-release drug delivery, Journal of Materials Chemistry B, Jan. 1, 2015, pp. 759-765, vol. 3, No. 5.
PCT International Search Report, PCT/EP2016/066583, dated Sep. 23, 2016.
PCT International Written Opinion, PCT/EP2016/066583, dated Sep. 23, 2016.
Sobolewski et al., Analogues of arginine vasopressin and its agonist and antagonist modified in the N-terminal part of the molecular with l-beta-homophenylalanine, Journal of Peptide Research, Apr. 1, 2005, pp. 465-471, vol. 65, No. 4.
PCT International Preliminary Report on Patentability, PCT/EP2016/066583, dated Jan. 25, 2018.
PCT International Search Report and Written Opinion, Application No. PCT/EP2017/053518, dated May 8, 2017.

* cited by examiner

*Primary Examiner* — Jeffrey E. Russel
(74) *Attorney, Agent, or Firm* — Patent Law Works LLP

(57) ABSTRACT

Provided are hydrogel-forming peptides that comprise at least one dyad of hydrophobic amino acid residues in which one is a $\beta^3$- or $\beta^2$-homo amino acid residue. The hydrogels derived from these peptides can be loaded with biological materials and can be used in physiological conditions.

15 Claims, No Drawings
Specification includes a Sequence Listing.

HYDROGEL-FORMING PEPTIDES

CROSS-REFERENCE TO RELATED APPLICATIONS

This application is a national phase entry under 35 U.S.C. § 371 of International Patent Application PCT/EP2016/066583, filed Jul. 13, 2016, designating the United States of America and published in English as International Patent Publication WO 2017/009358 A1 on Jan. 19, 2017, which claims the benefit under Article 8 of the Patent Cooperation Treaty to European Patent Application Serial No. 15176415.6, filed Jul. 13, 2015.

TECHNICAL FIELD

The present invention is situated in the field of hydrogels formed by defined peptides. More particularly, the invention provides hydrogel-forming peptides that comprise at least one dyad of hydrophobic amino acid residues in which one is a $\beta^3$- or $\beta^2$-homo amino acid residue. The hydrogels derived from these peptides can be loaded with active ingredients or biological materials.

BACKGROUND OF THE INVENTION

When administered orally or via another non-parenteral route many bioactive ingredients suffer from a poor pharmacokinetic profile due to fast elimination and metabolisation. Parenteral administration methods therefore are often the only option available. However multiple daily injections are often required in order to maintain steady-state supply of bioactive ingredients. This not only is cumbersome but also negatively impacts patient compliance. A solution to increase patient compliance is by reducing the number of injections to one per day, week or month by the use of controlled-drug delivery vehicles.

One option to achieve this goal is the incorporation of the bioactive ingredients into a hydrogel. Hydrogels are defined as three-dimensional physical or covalently cross-linked networks that are able to absorb a large amount of water while maintaining a semisolid morphology. The networks in hydrogels are able to retain up to 99.99% water making them very interesting candidates for carrying active ingredients and biomaterials. The hydrogel network can encapsulate and release therapeutics via various mechanisms, such as (de)swelling, external triggers: pH or temperature, erosion or diffusion. Hydrogel matrices moreover possess the capability to encapsulate and release therapeutics in a sustained manner over prolonged periods of time.

For biomedical applications, like tissue engineering, medical imaging or controlled drug delivery, the predominant class under investigation still remains the family of chemical hydrogels in which the polymeric network is held together by cross-links formed by chemical bonds. However, for in vivo applications these polymeric cross-linked structures often lack important requirements like stability in biological fluids, low toxicity and poor immunogenicity, especially when crosslinking is done in vivo.

Hydrogels prepared from cross-linked synthetic polymers possess various disadvantages such as (i) monomer and degradation product toxicity (e.g. toxic cross-linkers, like gluteraldehyde or local acidification due to degradation products of PLGA and analogues), (ii) in vivo uncontrollable polymer swelling can cause pain in the host, (iii) non-uniform polymers possess different pore sizes and concomitant different release properties, and (iv) unwanted burst effects and release of active ingredient over brief periods of time due to large pores in the polymer network. In addition most synthetic (chemically cross-linked) polymers can only be administered via minor surgery. Biopolymers such as collagen, gelatin and fibrin on the other hand do not possess clinical human applications due to their origin and the risk of inflammatory host response from viruses or bacteria.

To cope with the problems associated with hydrogels based on synthetic polymers, self-assembling peptide hydrogels have been developed as suitable alternatives to synthetic polymer hydrogels. Peptide based hydrogels are formed by molecular self-assembly of the native peptides to nanoscale fibers. Self-assembling peptide hydrogels offer interesting properties, such as shear-thinning, lack of in vivo toxicity and immunogenicity, good biocompatibility and biodegradability, making them fit for in vivo use with applications in the field of drug delivery and tissue engineering. The peptides can be readily prepared using standard peptide synthesis methods and by selection of the amino acid building blocks the amino acid sequence can be conveniently customized to tunable mechanical and release properties.

Various α-peptide sequences have been described as having hydrogel-forming properties under physiological conditions. Most of these possess an amphipatic structure wherein the peptide sequence either consists of alternating polar and apolar amino acids or contains a large hydrophobic end-group such as Fmoc.

Challenges in developing hydrogel-forming peptides are the selection of appropriate amino acids from the great diversity of available residues, their proneness to degradation by proteolytic enzymes, as well as the need to provide biocompatible, biodegradable and functional soft materials. A balance between hydrophobicity and hydrophilicity needs to be maintained when designing oligopeptide hydrogels in order to obtain a self-assembled system under suitable conditions. However, upon use of oligopeptide hydrogels as injectable controlled-delivery systems, challenges with regard to drug release rate, mechanism of release, determination of toxicity, fine-tuning of viscoelastic and release properties and assessing its biological stability still need to be addressed.

An important criterion for drug delivery from peptide hydrogels consists in an acceptable enzymatic stability to maintain sufficient control over the release of active components from a hydrogel matrix. In this context α-peptide hydrogelators that are easily cleaved by endo- and exopeptidases, could possess insufficient enzymatic stability leading to in vivo burst effects and destabilization of the supramolecular system. In addition, the previously mentioned amphipatic α-oligopeptides are reported to exhibit hours-to-days release profiles of various encapsulated compounds. However, these drug-delivery systems do not entirely meet the need for patients suffering from chronical diseases such as ALS, Alzheimer's disease, diabetes, and heart diseases. Indeed, longer term sustained delivery of pharmaceuticals is desirable, preferably during periods exceeding 24 hours such as several days or weeks. This not only would increase patient's comfort by decreasing the amount of injections required for efficient treatment, but also be beneficial in terms of compliance.

A growing area of interest for peptide hydrogels is that of tissue engineering, which involves the use of living cells as building blocks to repair or replace portions of or whole tissues, e.g. bone, cartilage, blood vessels, bladder, skin, muscle, etc. Cells are typically implanted or 'seeded' into an artificial structure capable of supporting three-dimensional tissue formation. These structures, called scaffolds, serve as support while mimicking the in vivo environment of the cells. Scaffolds can be made of different materials, which can be of natural or synthetic sources and can be biodegradable or not. Examples of natural materials include collagen and fibrin, and polysaccharidic materials, like chitosan or glycosaminoglycans (GAGs), while synthetic materials include biodegradable polyesters such as PLGA and its analogues. Hydrogel based scaffolds have been developed of which peptide based hydrogels have gained particular interest because of the properties mentioned above and in particular their good cell compatibility.

Although the current peptide based hydrogels offer attractive properties there still is room for improvement in particular as regards their mechanical and biological properties such as biocompatibility, improved immunogenicity and toxicity profile, as well as drug delivery characteristics.

Journal of Materials Chemistry B, 2015, 3, 759-765 describes an α-amino acid hexapeptide hydrogelator for controlled-release drug delivery. Angew. Chem. Int. Ed. 2013, 32, 8266-8270 reports 14-helical N-Acetyl-capped 3-peptides, which lead to supramolecular self-assembly resulting in nano- to macroscale fiber formation. Int. J. of Biological Macro. 2005, 36, 232-240 describes peptides with alternating hydrophobic and polar amino acids that form stable 3-sheet secondary structures and self-assemble into hydrogel-like matrices in the presence of physiological salt concentrations.

WO 2013/072686 describes self-assembling peptides α-amino acids that coalesce such that they self-assemble to form a hydrogel. US 2005/0181973 discloses self-assembling peptides of two-amino acid domains for use as scaffolds in cell culture, tissue engineering and tissue repair. US2014/0302144 discloses pharmaceutical formulations comprising self-assembling peptides for sustained delivery of therapeutic agents.

SUMMARY OF THE INVENTION

The present invention concerns peptides that form, preferably spontaneously, hydrogels under physiological conditions, which are meant to meet one or more of the needs recognized in the prior art, in particular those needs mentioned herein. It has been found that defined peptides containing dyads of hydrophobic amino acids in at least one of which a β-homo amino acid is present are capable of forming hydrogels that showed increased stability. The present invention concerns further aspects such as the hydrogels that can be formed from these 3-homo amino acid containing peptides, the preparation of these hydrogels, their various applications amongst which the use as drug-delivery platforms and scaffolds for biological materials, and other aspects.

Thus in one aspect there is provided a hydrogel-forming peptide, preferably a self-assembling hydrogel-forming peptide, that has from 5 to 12 amino acid residues, which amino acid residues are selected from hydrophobic and hydrophilic amino acid residues;

said peptide comprising one, two or three dyads of hydrophobic amino acid residues, wherein at least one dyad contains a β-homo amino acid residue, wherein each dyad and, if present, another dyad or another hydrophobic amino acid residue, are alternating with a hydrophilic amino acid residue;

wherein the amino acid residues that are not a 3-homo amino acid residue are α-amino acid residues;

wherein the N-terminus of the hydrogel-forming peptide bears one or two $R^a$ groups each independently selected from $R^1$, or bears one $R^1$ group and one group selected from $C(=Z)R^1$, $C(=Z)ZR^1$, $C(=Z)NHR^1$ and $C(=Z)N(R^1)_2$;

wherein each Z independently is O or S; and each $R^1$ is independently selected from H, optionally substituted linear or branched $C_{1-10}$alkyl, optionally substituted $C_{3-10}$cycloalkyl, optionally substituted aryl$C_{1-6}$alkyl and optionally substituted aryl; and wherein the C-terminus of the hydrogel-forming peptide bears one $R^b$ group selected from $OR^2$ or $N(R^2)_2$;

wherein each $R^2$ independently is selected from H, optionally substituted linear or branched $C_{1-10}$alkyl, optionally substituted $C_{3-10}$cycloalkyl, optionally substituted aryl$C_{1-6}$alkyl, and optionally substituted aryl;

or a salt form thereof.

In one embodiment the invention provides a hydrogel-forming peptide that can be represented by the following general formula I:

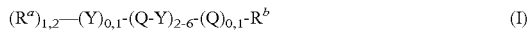

$$(R^a)_{1,2}-(Y)_{0,1}-(Q-Y)_{2-6}-(Q)_{0,1}-R^b \qquad (I)$$

wherein each Q independently is a hydrophobic amino acid residue or a dyad of hydrophobic amino acid residues; wherein one, two or three of said Q is a dyad of a hydrophobic α-amino acid residue and a β-homo amino acid residue;

each Y independently is a hydrophilic α-amino acid residue;

the group $(Y)_{0,1}$ represents a bond or a hydrophilic α-amino acid residue Y;

the group $(Q)_{0,1}$ represents a bond or a group Q;

$(R^a)_{1,2}$ represents one or two $R^a$ groups, substituted on the terminal nitrogen of said peptide, said $R^a$ groups are each independently selected from $R^1$, or $R^a$ groups represent one $R^1$ group and one group selected from $C(=Z)R^1$, $C(=Z)ZR^1$, $C(=Z)NHR^1$; $C(=Z)N(R^1)_2$;

wherein each Z independently is O or S; and each $R^1$ is independently selected from H, optionally substituted linear or branched $C_{1-10}$alkyl, optionally substituted $C_{3-10}$cycloalkyl, optionally substituted aryl$C_{1-6}$alkyl, and optionally substituted aryl;

$R^b$ is a group $OR^2$ or $N(R^2)_2$;

wherein each $R^2$ independently is selected from H, optionally substituted linear or branched $C_{1-10}$alkyl, optionally substituted $C_{3-10}$cycloalkyl, optionally substituted aryl$C_{1-6}$alkyl, and optionally substituted aryl;

wherein said peptide has from 5 to 12 amino acid residues;

or a salt form thereof.

In a further aspect, this invention concerns a hydrogel comprising a hydrogel-forming peptide, preferably a self-assembling hydrogel-forming peptide, as specified herein.

In still a further aspect, this invention concerns a composition comprising a hydrogel as specified herein and a biological material or a biologically active ingredient. The former may in particular include a cell, the latter an active pharmaceutical ingredient.

Still a further aspect of the invention relates to a process for preparing a hydrogel as specified herein, wherein a salt of a hydrogel-forming peptide as specified herein is dissolved in an aqueous medium containing a buffer, allowing the formation of the hydrogel to take place. The buffer preferably has a pH that is in the range of pH 6 to pH 8, more preferably about physiological pH.

DETAILED DESCRIPTION OF THE INVENTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +1-1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any ≥3, ≥4, ≥5, ≥6, or ≥7 etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

Whenever the term "substituted" is used herein, it is meant to indicate that one or more hydrogen atoms on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation from a reaction mixture.

As used herein $C_{1-10}$alkyl as a group or part of a group defines straight or branched chain saturated hydrocarbon groups having from 1 to 10 carbon atoms such as methyl, ethyl, 1-propyl, 2-propyl (iPr), 1-butyl, 2-methyl-1-propyl (i-Bu), 2-butyl (s-Bu), 2-dimethyl-2-propyl (t-Bu), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, pentyl and its isomers such as 2-methylbutyl, hexyl and its isomers such as 2-methylpentyl, heptyl and its isomers such as 2-methylhexyl, octyl, nonyl, decyl and their respective isomers, and the like.

Of interest amongst $C_{1-10}$alkyl is $C_{1-6}$alkyl, which is as specified above and has from 1 to 6 carbon atoms; of specific interest amongst $C_{1-6}$alkyl is $C_{1-4}$alkyl, which is as specified above and has from 1 to 4 carbon atoms; of interest amongst $C_{1-4}$alkyl is methyl or ethyl.

$C_3$-$C_{10}$cycloalkyl defines cyclic and, where possible, bicyclic saturated hydrocarbon groups having from 3 to 10 carbon atoms such as, e.g., cyclopropyl, cyclobutyl, cyclopentyl, cyclohexyl, cycloheptyl, cyclooctyl, cyclononyl, cyclodecyl, decalinyl. In one embodiment $C_3$-$C_{10}$cycloalkyl is monocyclic $C_3$-$C_7$cycloalkyl.

$C_{1-10}$alkyl and $C_3$-$C_{10}$cycloalkyl groups may be optionally substituted with one or more, in particular with 1, 2 or 3, substituents, which each independently may be selected from $C_{1-6}$alkyl, $C_3$-$C_7$cycloalkyl, halogen, $C_{1-6}$alkoxy, hydroxyl, amino, mono- and di-$C_{1-6}$alkyl amino, aryl, cyano, carboxyl, $C_{1-6}$alkylcarbonyl, $C_{1-6}$alkyloxycarbonyl, mercapto and $CF_3$. In one embodiment the substituents are selected from $C_{1-6}$alkyl, $C_3$-$C_7$cycloalkyl, halogen, $C_{1-6}$alkoxy, hydroxyl, amino, mono- and di-$C_{1-6}$alkyl amino, aryl, carboxyl, $C_{1-6}$alkylcarbonyl, $C_{1-6}$alkyloxycarbonyl.

The term "aryl" as used herein means an aromatic hydrocarbon radical of 6-14 carbon atoms such as phenyl, naphthalenyl, anthracenyl, biphenyl, and the like. Particular aryl groups are phenyl and naphthyl, especially phenyl.

An aryl group may be optionally substituted with one or more, in particular with 1, 2, 3, 4, or 5, or more in particular with 1, 2 or 3 substituents which each independently may be selected from $C_{1-6}$alkyl, $C_3$-$C_7$cycloalkyl, halogen, $C_{1-6}$alkoxy, hydroxyl, amino, mono- and di-$C_{1-6}$alkyl amino, aryl, nitro, cyano, carboxyl, $C_{1-6}$alkylcarbonyl, $C_{1-6}$alkyloxycarbonyl, azido, mercapto and $CF_3$.

The term "aryl$C_{1-6}$alkyl" as used herein refers to a $C_{1-6}$alkyl group substituted with an aryl group. In one embodiment the alkyl group is a $C_{1-4}$alkyl and the group is "aryl$C_{1-4}$alkyl". $C_{1-4}$alkyl and aryl are as specified herein. The aryl$C_{1-6}$alkyl group is linked to the rest of the molecule via a carbon atom of the alkyl moiety. Aryl$C_{1-6}$alkyl alkyl groups include benzyl, 2-phenylethyl, 1-phenylethyl, naphthylmethyl, 2-naphthylethyl, and the like.

The term "halogen" is generic to fluoro, chloro, bromo and iodo.

To avoid ambiguity it should be clear that the C-terminus of the peptides forms a group $COR^b$, the carbonyl in said group $COR^b$ is part of the C-terminal amino acid.

In a particular embodiment the N-terminus of the hydrogel-forming peptide bears one or two $R^a$ groups each independently selected from optionally substituted linear or branched $C_{1-10}$alkyl, or bears one hydrogen and one group selected from $C(=O)R^1$, $C(=O)OR^1$, $C(=O)NHR^1$ and $C(=O)N(R^1)_2$; and each $R^1$ is independently as specified herein.

In further embodiments each $R^1$ independently is H, linear or branched $C_{1-10}$alkyl, $C_{3-10}$cycloalkyl, aryl$C_{1-6}$alkyl or aryl. $R^1$ may also be phenyl or phenyl substituted with 1, 2 or 3 substituents selected from halogen, $C_{1-6}$alkyl and $C_{1-6}$alkyloxy.

In other embodiments each $R^1$ independently is H or linear or branched $C_{1-6}$alkyl. $R^1$ may be H or methyl.

In further embodiments one $R^a$ is H and the other $R^a$ is H, linear or branched $C_{1-10}$alkyl, or $C(=O)R^1$; in particular embodiments one $R^a$ is H and the other $R^a$ is H or $C(=O)R^1$; wherein in the latter $R^1$ is linear or branched $C_{1-6}$alkyl; or in particular embodiments one $R^a$ is H and the other $R^a$ is H or acetyl.

In other embodiments each $R^2$ independently is H, linear or branched $C_{1-10}$alkyl, $C_{3-10}$cycloalkyl, aryl$C_{1-6}$alkyl or phenyl optionally substituted with 1, 2 or 3 substituents selected from halogen, $C_{1-6}$alkyl and $C_{1-6}$alkyloxy. In particular embodiments each $R^2$ independently is H, linear or branched $C_{1-6}$alkyl, benzyl or phenyl.

In certain embodiments $R^b$ is a group $OR^2$ wherein $R^2$ is H or linear or branched $C_{1-6}$alkyl; or $R^b$ is a group $N(R^2)_2$ wherein each $R^2$ independently is H or linear or branched $C_{1-6}$alkyl.

In one embodiment one $R^a$ is hydrogen and the other $R^a$ is hydrogen or $C_{1-4}$alkylcarbonyl.

In certain embodiments $R^b$ is hydroxyl, amino ($NH_2$), $C_{1-6}$alkylNH—, $(C_{1-6}alkyl)_2NH$—; in particular $R^b$ is OH, amino or aminomethyl. In particular embodiments $R^b$ is OH or $NH_2$.

Embodiments of the invention concern those peptides either wherein each $R^a$ is H and/or wherein $R^b$ is OH or $NH_2$.

The peptides disclosed herein are amphipatic in nature containing a linear sequence of amino acid residues derived from hydrophobic amino acids and hydrophilic amino acids linked by peptide bonds.

The term "hydrophobic amino acids" refers to naturally occurring amino acids having a hydrophobic and/or aromatic side chain, such as alanine, valine, leucine, isoleucine, and the aromatic amino acids phenylalanine, tyrosine and tryptophan. Further included is the non-natural amino acid cyclohexylalanine. Other examples include ring-substituted phenylalanine, tyrosine or tryptophan derivatives (including e.g. fluoro/chloro/bromo/iodo/cyano-phenylalanine, o.tyrosine, m.tyrosine, fluoro-tryptophan, hydroxy-tryptophan, methoxy-tryptophan). The hydrophobic amino acids can have an R (right) or S (left) enantiomeric configuration. The R/S notation is determined by the Cahn-Ingold-Prelog priority rules based on the atomic number of the four atoms directly attached to the stereogenic center.

The term "hydrophilic amino acids" refers to amino acids having a hydrophilic side chain; such side chain may be uncharged, positively (cationic) or negatively charged (anionic) under normal physiological conditions, in particular at about pH 7.4. Uncharged hydrophilic amino acids include asparagine and glutamine; positively charged hydrophilic amino acids include arginine, histidine and lysine, and the non-natural amino acid ornithine; negatively charged amino acids include aspartic acid and glutamic acid. The hydrophilic amino acids can have an R (right) or S (left) enantiomeric configuration. The R/S notation is determined by the Cahn-Ingold-Prelog priority rules based on the atomic number of the four atoms directly attached to the stereogenic center.

The amino acid residues preferably are L-amino acid residues.

As used herein the term "dyad" refers to a pair of adjacent amino acid residues linked by a peptide bond. In a hydrophobic dyad both amino acid residues are hydrophobic. At least one dyad contains a hydrophobic β-homo amino acid ("β-h" or "β" amino acid). In one embodiment all hydrophobic dyads contain a hydrophobic β-homo amino acid.

Each dyad and, if present, another dyad or another hydrophobic amino acid residue, are alternating with a hydrophilic amino acid residue. This means that each dyad is linked to another dyad, if present, or to another hydrophobic amino acid residue, if present, by a hydrophilic amino acid residue.

Hydrophobic β-homo amino acids are structural analogues of α-amino acids wherein a methylene group has been inserted in the backbone. These include two variants. A first group concerns β³-homo amino acids in which a methylene group has been inserted between the carbon atom bearing the side-chain and the carboxyl group. A second group concerns β²-homo amino acids wherein a methylene group has been inserted between the carbon atom bearing the side-chain and the amino group. Of interest are hydrophobic β³-homo amino acids. β³-homo- and β²-homo amino acids are referred to herein as "β³-" and "β²-" amino acids or "β³h-" and "β²h-" amino acids, in particular in the sequences. For example, β³homo-Phe-Phe- can be referred to herein as β³Phe-Phe- or β³hPhe-Phe-.

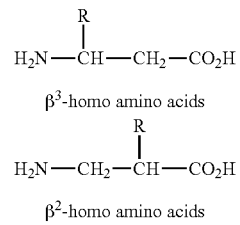

β³-homo amino acids

β²-homo amino acids

β-homo amino acids for use in the invention are the β²- and β³-homologues of the hydrophobic α-amino acids mentioned above such as, for example, β³-homoalanine, β³-homovaline, β³-homoisoleucine, β³-homoleucine, and in particular β³-homophenylalanine, β³-homotryptophan and β³-homotyrosine; as well as β²-homoalanine, β²-homovaline, β²-homoisoleucine, β²-homoleucine, and in particular β²-homophenylalanine, β²-homotryptophan and β²-homotyrosine. The β-homo amino acids can have an R or S enantiomeric configuration.

In the dyads containing a hydrophobic β³-homo amino acid, the latter may be positioned at the side closest to the C-terminus of the peptide, or, which is preferred, may be positioned at the side closest to the N-terminus of the peptide. In the dyads containing a hydrophobic β²-homo amino acid, the latter may be positioned at the side closest to the N-terminus of the peptide, or, which is preferred, may be positioned at the side closest to the C-terminus of the peptide.

As used herein the group $(Q-Y)_{2-6}$ refers to a group that has two, three, four, five or six consecutive Q-Y groups. In each of these Q-Y groups each Q and each Y independently are as specified herein. For example a group $(Q-Y)_2$ may represent a sequence Q-Y-Q-Y, which includes D-Y-D-Y, X—Y-D-Y, D-Y—X—Y, X—Y—X—Y, in which D is dyad as specified herein; each X independently is a hydrophobic amino acid residue, and Y is a hydrophilic amino acid residue.

In embodiments of the invention, the hydrogel forming peptides, preferably self-assembling hydrogel-forming peptides, are those of the above mentioned formula I: $(R^a)_{1,2}$—$(Y)_{0,1}$-$(Q-Y)_{2-6}$-$(Q)_{0,1}$-$R^b$, or a salt thereof, wherein one or more of the following apply:

at least one Y group is a charged amino acid residue at physiological pH; or when at least two Y groups are present, they bear the same or, which is preferred, opposite charges at physiological pH;

—$(Y)_{0,1}$— is a bond;

-$(Q)_{0,1}$- is a bond;

-$(Q-Y)_{2-6}$— is -$(Q-Y)_{2-4}$—; wherein one or two Q groups represent a dyad as specified herein;

at least one Y is a negatively charged, or is a neutral, or is a positively charged amino acid residue;

wherein charged means charged at physiological pH.

In one embodiment, the peptides are pentapeptides containing one dyad of a hydrophobic β-homo amino acid and an α-amino acid; or the peptides are hexa- or heptapeptides containing one or two dyads of a hydrophobic β-homo amino acid and an α-amino acid, or octa-, nona-, deca- undeca, dodecapeptides containing one, two or three dyads of a hydrophobic β-homo amino acid and an α-amino acid.

Embodiments of the invention are those hydrogel-forming peptides of formula I, preferably self-assembling hydrogel-forming peptides, wherein
—(Y)$_{0,1}$— is a bond;
the first Q-Y group represents a group —X—Y—, wherein X is Phe, Tyr, or Trp; Y is Glu, Gln, Asp or Asn;
two, three or four -(Q-Y)— groups are present, wherein one, two or three Q groups is a dyad; in particular wherein each dyad independently is of formula -β$^3$-homo-Phe-Phe-, or -β$^3$-homo-Phe-Tyr-; and each Y independently is Lys, Glu, Gln, Asp or Asn; and -(Q)$_{0,1}$- is a bond.

Embodiments of the invention are those hydrogel-forming peptides of formula I, preferably self-assembling hydrogel-forming peptides, wherein the peptide is a pentapeptide wherein:
—(Y)$_{0,1}$— is a bond;
the first Q-Y group represents a group —X—Y—, wherein X is Phe, Tyr, or Trp; Y is Glu, Gln, Asp or Asn;
in the second Q-Y group Q is a dyad, which dyad is of formula -β$^3$-homo-Phe-Phe- or -β$^3$-homo-Phe-Tyr- and Y in said second Q-Y group independently is Lys, Glu, Gln, Asp or Asn;
-(Q)$_{0-1}$- is a bond.

Embodiments of the invention are those hydrogel-forming peptides of formula I, preferably self-assembling hydrogel-forming peptides, wherein the peptide is a hexapeptide wherein:
—(Y)$_{0,1}$— is a bond;
the first Q-Y group represents a group —X—Y—, wherein X is Phe, Tyr, or Trp; Y is Glu, Gln, Asp or Asn;
in the second Q-Y group Q is a dyad, which dyad is of formula -β$^3$-homo-Phe-Phe-, or -β$^3$-homo-Phe-Tyr- and Y in said second Q-Y group independently is Lys, Glu, Gln, Asp or Asn;
-(Q)$_{0-1}$- is X.

Embodiments of the invention are those hydrogel-forming peptides of formula I, preferably self-assembling hydrogel-forming peptides, wherein the peptide is a heptapeptide wherein:
—(Y)$_{0,1}$— is a bond;
the first Q-Y group represents a group —X—Y—, wherein X is Phe, Tyr or Trp; Y is Glu, Gln, Asp or Asn;
in the second or third Q-Y group one Q is a dyad, which dyad is of formula -β$^3$-homo-Phe-Phe-, or -β$^3$-homo-Phe-Tyr- and Y in said second or third Q-Y group independently is Lys, Glu, Gln, Asp or Asn;
-(Q)$_{0,1}$- is a bond.

Embodiments of the invention are those hydrogel-forming peptides of formula I, preferably self-assembling hydrogel-forming peptides, wherein the peptide is a octapeptide wherein:
—(Y)$_{0,1}$— is a bond;
the first Q-Y group represents a group —X—Y—, wherein X is Phe, Tyr or Trp; Y is Glu, Gln, Asp or Asn;
in the second or third Q-Y group one or two of Q is a dyad, which dyad is of formula -β$^3$-homo-Phe-Phe-, or -β$^3$-homo-Phe-Tyr- and Y in said second or third Q-Y group independently is Lys, Glu, Gln, Asp or Asn;
-(Q)$_{0,1}$- is a bond or X.

Particular hydrogel-forming peptides include those of formula II, $$(R^a)_{1,2}\text{-AA-}R^b \qquad (II)$$

or a salt thereof,
wherein $(R^a)_{1,2}$ and $R^b$ are as specified herein, and AA represents a peptide sequence of amino acid residues selected from the following, in which each X independently is a hydrophobic amino acid residue; each Y independently is a hydrophilic amino acid residue; each D independently is a dyad of a hydrophobic β-homo amino acid residue and a hydrophobic/aromatic α-amino acid residue; wherein the sequence of said hydrophobic amino acid residue, hydrophilic amino acid residue and dyad of a hydrophobic β-homo amino acid residue and a hydrophobic/aromatic α-amino acid residue can be represented as in the following examples:

| Pentapeptides: | | |
|---|---|---|
| D-Y-X-Y | | |
| Y-D-Y-X | | |
| X-Y-D-Y | | |
| Y-X-Y-D | | |

| Hexapeptides | | |
|---|---|---|
| D-Y-X-Y-X | D-Y-D-Y | |
| Y-D-Y-X-Y | Y-D-Y-D | |
| X-Y-D-Y-X | | |
| Y-X-Y-D-Y | | |
| X-Y-X-Y-D | | |

| Heptapeptides | | |
|---|---|---|
| D-Y-X-Y-X-Y | D-Y-D-Y-X | |
| Y-D-Y-X-Y-X | Y-D-Y-D-Y | |
| X-Y-D-Y-X-Y | X-Y-D-Y-D | |
| Y-X-Y-D-Y-X | D-Y-X-Y-D | |
| X-Y-X-Y-D-Y | | |
| Y-X-Y-X-Y-D | | |

| Octapeptides | | |
|---|---|---|
| D-Y-X-Y-X-Y-X | D-Y-D-Y-X-Y | D-Y-D-Y-D |
| Y-D-Y-X-Y-X-Y | Y-D-Y-D-Y-X | |
| X-Y-D-Y-X-Y-X | X-Y-D-Y-D-Y | |
| Y-X-Y-D-Y-X-Y | Y-X-Y-D-Y-D | |
| X-Y-X-Y-D-Y-X | D-Y-X-Y-D-Y | |
| Y-X-Y-X-Y-D-Y | Y-D-Y-X-Y-D | |
| X-Y-X-Y-X-Y-D | | |

| Nonapeptides | | |
|---|---|---|
| D-Y-X-Y-X-Y-X-Y | D-Y-D-Y-X-Y-X | D-Y-D-Y-D-Y |
| Y-D-Y-X-Y-X-Y-X | Y-D-Y-D-Y-X-Y | Y-D-Y-D-Y-D |

| | | |
|---|---|---|
| X-Y-D-Y-X-Y-X-Y | X-Y-D-Y-D-Y-X | |
| Y-X-Y-D-Y-X-Y-X | Y-X-Y-D-Y-D-Y | |
| X-Y-X-Y-D-Y-X-Y | X-Y-X-Y-D-Y-D | |
| Y-X-Y-X-Y-D-Y-X | D-Y-X-Y-D-Y-X | |
| X-Y-X-Y-X-Y-D-Y | Y-D-Y-X-Y-X-D-Y | |
| Y-X-Y-X-Y-X-Y-D | X-Y-D-Y-X-Y-D | |
| | D-Y-X-Y-X-Y-D | |

Decapeptides

| | | |
|---|---|---|
| D-Y-X-Y-X-Y-X-Y-X | D-Y-D-Y-X-Y-X-Y | D-Y-D-Y-D-Y-Y-X |
| Y-D-Y-X-Y-X-Y-X-Y | Y-D-Y-D-Y-X-Y-X | Y-D-Y-D-Y-D-Y |
| X-Y-D-Y-X-Y-X-Y-X | X-Y-D-Y-D-Y-X-Y | X-Y-D-Y-D-Y-D |
| Y-X-Y-D-Y-X-Y-X-Y | Y-X-Y-D-Y-D-Y-X | D-Y-X-Y-D-Y-D |
| X-Y-X-Y-D-Y-X-Y-X | X-Y-X-Y-D-Y-D-Y | D-Y-D-Y-X-Y-D |
| Y-X-Y-X-Y-D-Y-X-Y | Y-X-Y-X-Y-D-Y-D | |
| X-Y-X-Y-X-Y-D-Y-X | D-Y-X-Y-D-Y-X-Y | |
| Y-X-Y-X-Y-X-Y-D-Y | Y-D-Y-X-Y-D-Y-X | |
| X-Y-X-Y-X-Y-X-Y-D | X-Y-D-Y-X-Y-D-Y | |
| | Y-X-Y-D-Y-X-Y-D | |
| | D-Y-X-Y-X-Y-D-Y | |
| | Y-D-Y-X-Y-X-Y-D | |

Undecapeptides

| | | |
|---|---|---|
| D-Y-X-Y-X-Y-X-Y-X-Y | D-Y-D-Y-X-Y-X-Y-X | D-Y-D-Y-D-Y-X-Y |
| Y-D-Y-X-Y-X-Y-X-Y-X | Y-D-Y-D-Y-X-Y-X-Y | Y-D-Y-D-Y-D-Y-X |
| X-Y-D-Y-X-Y-X-Y-X-Y | X-Y-D-Y-D-Y-X-Y-X | X-Y-D-Y-D-Y-D-Y |
| Y-X-Y-D-Y-X-Y-X-Y-X | Y-X-Y-D-Y-D-Y-X-Y | Y-X-Y-D-Y-D-Y-D |
| X-Y-X-Y-D-Y-X-Y-X-Y | X-Y-X-Y-D-Y-D-Y-X | D-Y-D-Y-X-Y-D-Y |
| Y-X-Y-X-Y-D-Y-X-Y-X | Y-X-Y-X-Y-D-Y-D-Y | D-Y-X-Y-D-Y-D-Y |
| X-Y-X-Y-X-Y-D-Y-X-Y | X-Y-X-Y-X-Y-D-Y-D | Y-D-Y-D-Y-X-Y-D |
| Y-X-Y-X-Y-X-Y-D-Y-X | D-Y-X-Y-D-Y-X-Y-X | |
| X-Y-X-Y-X-Y-X-Y-D-Y | Y-D-Y-X-Y-D-Y-X-Y | |
| Y-X-Y-X-Y-X-Y-X-Y-D | X-Y-D-Y-X-Y-D-Y-X | |
| | Y-X-Y-D-Y-X-Y-D-Y | |
| | X-Y-X-Y-D-Y-X-Y-D | |
| | D-Y-X-Y-X-Y-D-Y-X | |
| | Y-D-Y-X-Y-X-Y-D-Y | |
| | X-Y-D-Y-X-Y-X-Y-D | |
| | D-Y-X-Y-X-Y-X-Y-D | |

Dodecapeptides

| | | |
|---|---|---|
| D-Y-X-Y-X-Y-X-Y-X-Y-X | D-Y-D-Y-X-Y-X-Y-X-Y | D-Y-D-Y-D-Y-X-Y-X |
| Y-D-Y-X-Y-X-Y-X-Y-X-Y | Y-D-Y-D-Y-X-Y-X-Y-X | Y-D-Y-D-Y-D-Y-X-Y |
| X-Y-D-Y-X-Y-X-Y-X-Y-X | X-Y-D-Y-D-Y-X-Y-X-Y | X-Y-D-Y-D-Y-D-Y-X |
| Y-X-Y-D-Y-X-Y-X-Y-X-Y | Y-X-Y-D-Y-D-Y-X-Y-X | Y-X-Y-D-Y-D-Y-D-Y |
| X-Y-X-Y-D-Y-X-Y-X-Y-X | X-Y-X-Y-D-Y-D-Y-X-Y | X-Y-X-Y-D-Y-D-Y-D |
| Y-X-Y-X-Y-D-Y-X-Y-X-Y | Y-X-Y-X-Y-D-Y-D-Y-X | D-Y-D-Y-X-Y-D-Y-X |
| X-Y-X-Y-X-Y-D-Y-X-Y-X | X-Y-X-Y-X-Y-D-Y-D-Y | Y-D-Y-D-Y-X-Y-D-Y |
| Y-X-Y-X-Y-X-Y-D-Y-X-Y | Y-X-Y-X-Y-X-Y-D-Y-D | X-Y-D-Y-D-Y-X-Y-D |
| X-Y-X-Y-X-Y-X-Y-D-Y-X | D-Y-X-Y-D-Y-X-Y-X-Y | D-Y-X-Y-D-Y-D-Y-X |
| Y-X-Y-X-Y-X-Y-X-Y-D-Y | Y-D-Y-X-Y-D-Y-X-Y-X | Y-D-Y-X-Y-D-Y-D-Y |
| X-Y-X-Y-X-Y-X-Y-X-Y-D | X-Y-D-Y-X-Y-D-Y-X-Y | X-Y-D-Y-X-Y-D-Y-D |
| | Y-X-Y-D-Y-X-Y-D-Y-X | D-Y-X-Y-X-Y-D-Y-D |
| | X-Y-X-Y-D-Y-X-Y-D-Y | |
| | Y-X-Y-X-Y-D-Y-X-Y-D | |
| | D-Y-X-Y-X-Y-D-Y-X-Y | |
| | Y-D-Y-X-Y-X-Y-D-Y-X | |
| | X-Y-D-Y-X-Y-X-Y-D-Y | |
| | Y-X-Y-D-Y-X-Y-X-Y-D | |
| | D-Y-X-Y-X-Y-X-Y-D-Y | |
| | Y-D-Y-X-Y-X-Y-X-Y-D | |

In each of said exemplary peptides, the N-terminus and C-terminus can be independently substituted with respectively $R^a$ and $R^b$ as defined herein; and In each of said exemplary peptides, said one or more dyad(s) (D) can be formed by a hydrophobic $\beta^3$-homo amino acid residue followed by a hydrophobic/aromatic α-amino acid residue, or by a hydrophobic/aromatic α-amino acid residue followed by a hydrophobic $\beta^2$-homo amino acid residue.

Particular hydrogel-forming peptides, preferably self-assembling hydrogel-forming peptides, include the following:

(SEQ ID NO. 1)
H-FEβ³hFFQβ³hFFK-OH (H-Phe-Glu-β³hPhe-Phe-Gln-β³hPhe-Phe-Lys-OH), (SEQ ID NO. 2)
H-FEβ³hFFQβ³hFFK-NH₂, (H-Phe-Glu-β³hPhe-Phe-Gln-β³hPhe-Phe-Lys-NH₂), (SEQ ID NO. 3)
H-FEβ³hFYQβ³hFYK-NH₂, (H-Phe-Glu-β³hPhe-Tyr-Gln-β³hPhe-Tyr-Lys-NH₂),

-continued (SEQ ID NO. 4)
H-FEβ³hFYQβ³hFYK-OH, (H-Phe-Glu-β³Phe-Tyr-Gln-β³hPhe-Tyr-Lys-OH), (SEQ ID NO. 5)
H-FQβ³hFFQβ³hFFK-OH (H-Phe-Gln-β³hPhe-Phe-Gln-β³hPhe-Phe-Lys-OH), (SEQ ID NO. 6)
H-FEβ³hFFK-NH$_2$, (H-Phe-Glu-β³hPhe-Phe-Lys-NH$_2$), (SEQ ID NO. 7)
H-FEβ³hFFK-OH, (H-Phe-Glu-β³hPhe-Phe-Lys-OH), (SEQ ID NO. 8)
H-FEβ³hChaFQβ³hChaFK-OH, (H-Phe-Glu-β³hCha-Phe-Gln-β³hCha-Phe-Lys-OH), (SEQ ID NO. 9)
H-FQβ³hFFK-NH$_2$ (H-Phe-Gln-β³hPhe-Phe-Lys-NH$_2$), (SEQ ID NO. 10)
H-β³hFFEβ³hFFK-NH$_2$, (H-β³hPhe-Phe-Glu-β³hPhe-Phe-Lys-NH$_2$), (SEQ ID NO. 11)
H-FEβ³hFFKF-NH$_2$ (H-Phe-Glu-β³hPhe-Phe-Lys-Phe-NH$_2$), (SEQ ID NO. 12)
H-Eβ³hFFKβ³hFF-NH$_2$ (H-Glu-β³hPhe-Phe-Lys-β³hPhe-Phe-NH$_2$), (SEQ ID NO. 13)
H-FEβ³hFFQFK-NH$_2$ (H-Phe-Glu-β³hPhe-Phe-Gln-Phe-Lys-NH$_2$), (SEQ ID NO. 14)
H-WEβ³hWWQWK-NH$_2$ (H-Trp-Glu-β³hTrp-Trp-Gln-Trp-Lys-NH$_2$), (SEQ ID NO. 15)
H-WEβ³hFFQWK-NH$_2$ (H-Trp-Glu-β³hPhe-Phe-Gln-Trp-Lys-NH$_2$), (SEQ ID NO. 16)
H-FEβ³hFFKβ³hFF-NH$_2$ (H-Phe-Glu-β³hPhe-Phe-Lys-β³hPhe-Phe-NH$_2$), (SEQ ID NO. 17)
H-β³hFFEFQFK-NH$_2$ (H-β³hPhe-Phe-Glu-Phe-Gln-Phe-Lys-NH$_2$), (SEQ ID NO. 18)
H-FEFQβ³hFFK-NH$_2$ (H-Phe-Glu-Phe-Gln-β³hPhe-Phe-Lys-NH$_2$), (SEQ ID NO. 19)
H-Fβ³hFEFQFK-NH$_2$ (H-Phe-β³hPhe-Glu-Phe-Gln-Phe-Lys-NH$_2$), (SEQ ID NO. 20)
H-FEβ³hFFQFKF-NH$_2$ (H-Phe-Glu-β³hPhe-Phe-Gln-Phe-Lys-Phe-NH$_2$), (SEQ ID NO. 21)
H-FEFQFKβ³hFF-NH$_2$ (H-Phe-Glu-Phe-Gln-Phe-Lys-β³hPhe-Phe-NH$_2$), (SEQ ID NO. 22)
H-FEβ³hFFQFQβ³hFFK-NH$_2$ (H-Phe-Glu-β³hPhe-Phe-Gln-Phe-Gln-β³hPhe-Phe-Lys-NH$_2$);
or or a salt-form thereof.

Of interest are the free forms or the trifluoroacetate salts of the above peptides.

Of particular interest are the peptides with SEQ ID NO. 1, 2, 3, 6 and 9, or the trifluoroacetate salts thereof.

Salt-forms of the hydrogel-forming peptides include, where possible, acid addition and base addition salt forms. Preferred are those that are pharmaceutically acceptable. The pharmaceutically acceptable acid addition salts can conveniently be obtained by treating the peptides having a basic group with such appropriate acid. Appropriate acids comprise, e.g., inorganic acids such as hydrohalic acids, e.g. hydrochloric or hydrobromic acid, sulfuric, nitric, and phosphoric acid; or organic acids such as acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid. The peptides containing an acidic proton may also be converted into their metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts. Of particular interest are the trifluoroacetate salts.

The hydrogel-forming peptides described herein can be synthesized according to art-known methods of liquid phase or solid phase peptide synthesis by single amino acid coupling, fragment condensation or a combination thereof. Cleavage of synthesized peptides from a resin in solid phase peptide synthesis, removal of protecting groups and purification of peptides are well known in the art. Cleavage of synthesized peptides from a resin in solid phase synthesis can be done, for example, by trifluoroacetic acid. The synthesized peptides can be purified, e.g., by chromatography such as HPLC. For example, the peptides can be synthesized by solid phase methodology using standard coupling methods using t-butyloxycarbonyl (Boc) or 9-fluorenylmethoxy-carbonyl (Fmoc) protecting groups.

The peptides of the invention are self-assembling. In aqueous media they spontaneously form supramolecular assemblies, which eventually lead to the formation of hydrogel networks.

The invention further concerns hydrogels comprising a hydrogel-forming peptide, preferably self-assembling, as specified herein.

The hydrogels can be prepared from the present gel-forming peptides by allowing them to self-assemble leading to the formation of a hydrogel. Thus the invention further concerns a process for preparing a hydrogel comprising a hydrogel-forming peptide as specified herein, wherein the process comprises dissolving the hydrogel-forming peptide, or preferably, an acid addition salt thereof, in an aqueous medium, and allowing the hydrogel-forming peptide to assemble in the presence of a buffer having a pH that is in the range of pH 5 to pH 9, to obtain a self-sustaining hydrogel.

A concentration of 0.1 to 10% w/v, more particularly of 0.5 to 5% w/v, in particular of 2 to 3% w/v, of peptide or peptide salt may be used to form self-sustaining hydrogels.

Particular hydrogel-forming peptides have the following preferred gelation conditions:

| Sequence | Gelation condition % (w/v) | SEQ ID NO |
|---|---|---|
| H-FEβ³hFFQβ³hFFK-OH | 2% (mQ) | SEQ ID NO: 01 |
| H-FEβ³hFFQβ³hFFK-NH$_2$ | 2% (mQ/PBS 1:1) | SEQ ID NO: 02 |
| H-FEβ³hFYQβ³hFYK-NH$_2$ | 2.5% (PBS) | SEQ ID NO: 03 |
| H-FEβ³hFYQβ³hFYK-OH | 2% (PBS) | SEQ ID NO: 04 |
| H-FQβ³hFFQβ³hFFK-OH | 2% (mQ) | SEQ ID NO: 05 |
| H-FEβ³hFFK-NH$_2$ | 3% (PBS) | SEQ ID NO: 06 |
| H-FEβ³hFFK-OH | 3% (mQ) | SEQ ID NO: 07 |
| H-FEβ³hChaFQβ³hChaFK-OH | 3% (mQ) | SEQ ID NO: 08 |
| H-FQβ³hFFK-NH$_2$ | 3% (PBS) | SEQ ID NO: 09 |
| H-β³hFFEβ³hFFK-NH$_2$ | 1% (PBS) | SEQ ID NO: 10 |
| H-FEβ³hFFKF-NH$_2$ | 2% (PBS) | SEQ ID NO: 11 |
| H-Eβ³hFFKβ³hFF-NH$_2$ | 1.5% (mQ/PBS 1:0.5) | SEQ ID NO: 12 |
| H-FEβ³hFFQFK-NH$_2$ | 2% (PBS) | SEQ ID NO: 13 |
| H-WEβ³hWWQWK-NH$_2$ | 1.5% (mQ/PBS 1:0.5) | SEQ ID NO: 14 |
| H-WEβ³hFFQWK-NH$_2$ | 2% (PBS) | SEQ ID NO: 15 |
| H-FEβ³hFFKβ³hFF-NH$_2$ | 2% (mQ) | SEQ ID NO: 16 |
| H-β³hFFEFQFK-NH$_2$ | 2% (PBS) | SEQ ID NO: 17 |
| H-FEFQβ³hFFK-NH$_2$ | 2% (PBS) | SEQ ID NO: 18 |
| H-Fβ³hFEFQFK-NH$_2$ | 2% (PBS) | SEQ ID NO: 19 |
| H-FEβ³hFFQFKF-NH$_2$ | 1.5% (mQ/PBS 1:1) | SEQ ID NO: 20 |
| H-FEFQFKβ³hFF-NH$_2$ | 1.5% (mQ/PBS 1:1) | SEQ ID NO: 21 |
| H-FEβ³hFFQFQβ³hFFK-NH$_2$ | 2% (mQ) | SEQ ID NO: 22 |

Aqueous media include water, in particular purified water such as mQ water; which water or purified water (such as mQ water) may contain a buffer. The pH of the buffer may be as mentioned above or may be in the range of pH 6 to pH 8.5, in particular in the range of pH 7 to pH 8. In one embodiment the buffer has a pH that is about physiological pH, in particular a pH that is about 7.4.

Buffers that can be used include phosphate buffers, in particular $HPO_4/H_2PO_4^-$ based buffers wherein the counter ions are $Na^+$ or $K^+$, borate buffers, tris(hydroxymethyl)-aminomethane (Tris) buffers in particular Tris/HCl buffers, bicarbonate buffers, citrate buffers, and the like. The buffers may be supplemented with one or more salts such as sodium or potassium chloride or a combination thereof. The buffer can be a pre-prepared buffer solution, which may further contain one or more salts. An example is the so-called phosphate buffer saline (PBS), Tris buffer saline (TBS) or physiological saline solution (0.9% NaCl). Preferably, PBS (pH 7.4) or physiological saline solution (0.9% NaCl) is used as a buffer.

In a particular embodiment the buffer is PBS and the aqueous medium is purified water (so-called mQ water). The PBS preferably is used at a concentration that is in the range of 5 to 20 mM ions, in particular of 5 to 15 mM ions, more in particular the concentration is about 10 mM ions. Hydrogels prepared using PBS are particularly interesting for use as carriers of biomaterials and active ingredients due to the buffering effect of PBS (to physiological pH) and the isotonic relation to the human body.

The hydrogel-forming peptides according to the invention can self-assemble into hydrogels instantaneously, within minutes, in 1 hour, in 2 hours, in 3 hours, in 4 hours, in 5 hours, in 6 hours, in 7 hours, in 8 hours, in 9 hours or in 10 hours, preferably instantaneously, i.e. in less than 2 hours, preferably in less than 1 hour, more preferably within 30 minutes.

The structure of the self-assembled hydrogels can be analyzed by circular dichroism (CD) and Fourier transform infrared (FT-IR) spectroscopy, as well as cryogenic transmission electron microscopy (Cryo-TEM).

The hydrogels of the invention can be used as carriers for various biologically active ingredients as well as biological materials. Thus the invention provides compositions comprising a hydrogel as described herein and one or more biological materials or one or more biologically active ingredients, or a combination thereof.

As used herein, the term "biologically active ingredient" (sometimes also referred to as "active ingredient") is meant to include ingredients or agents that are biologically active. Also covered by these terms are diagnostic agents as well as so-called "cosmeceuticals". Diagnostic agents include, for example, fluorescent proteins (e.g. green fluorescent protein or GFP) or radiolabeled molecules. Cosmeceuticals include active ingredients that have an effect on the outer appearance of an individual such as on skin, hair, lips, and eyes, and encompass anti-wrinkling agents and agents that improve complexion. In these applications the hydrogels preferably are administered externally. Active pharmaceutical ingredients (also referred to as drugs) are of particular interest and form a subgroup of biologically active ingredients.

The biologically active ingredients may include small molecules (such as those having a molecular weight of less than about 1,500), synthetic or natural such as monosaccharides, disaccharides, trisaccharides, oligosaccharides, peptides, nucleic acids but also nucleic acid analogues and derivatives; or large molecules, including plasmids, vectors, polysaccharides, biological macromolecules, e.g., larger peptides (polypeptides), proteins, peptide analogues and derivatives thereof, peptidomimetics, nucleic acid based molecules (e.g. DNA, RNA, mRNA, tRNA, RNAi, siRNA, microRNA, or any other DNA or RNA-like molecules), polynucleotides, oligonucleotides, enzymes, antibiotics, extracts made from biological materials such as bacteria, plants, fungi, or animal cells or tissues, therapeutic agents, preventatives, diagnostic agents, imaging agents, aptamers (including oligonucleotide or protein aptamers).

In one embodiment the biologically active ingredients are water-soluble, particularly are water-soluble active pharmaceutical ingredients. Such ingredients may belong to Class I or III of the Biopharmaceutical Classification System (BCS), which classifies drug substances into four classes: Class I—High Permeability, High Solubility; Class II—High Permeability, Low Solubility; Class III—Low Permeability, High Solubility; Class IV—Low Permeability, Low Solubility. Water-soluble drugs can also be specified by the amount of a water (g) required to solve 1 g of a compound, wherein water-soluble drugs are those fulfilling the following solubility qualifications: 10-30 g ("soluble"); 30-100 g ("sparingly soluble"); 100-1000 g ("slightly soluble"); 1000-10000 g ("very slightly soluble" or "poorly soluble"); or particularly soluble, sparingly soluble and slightly soluble drugs.

Drugs that can be incorporated in the hydrogels of the invention include those used in the treatment of diseases related to the nervous system such as ALS, Alzheimer's disease, Parkinson's disease; psychotherapeutic diseases such as bipolar disorder, anxiety, depression; metabolic diseases such as diabetes (e.g. insulin) and hypolipemic agents; infectious diseases such as antifugals, antibiotics, antivirals such as to treat HIV or HCV; cardiovascular conditions such as antihypertensives; anti-acne agents; anti-allegic agents; anti-asthmatics; anticancer agents; hormonal contraceptives; analgesics; agents to treat sleep disorders and overweight; anti-inflammatories; mucolytics; antitussives; antiulceratives.

Of interest for incorporation into the hydrogels are drugs that are used in the treatment of chronical diseases.

In one embodiment the biologically active ingredients are antibodies or antibody fragments. The term "antibody" is meant to include monoclonal antibodies, polyclonal antibodies and multispecific antibodies (e.g. bispecific antibodies). Antibody fragments comprise a portion of an antibody, generally the antigen binding or variable region thereof. Examples of antibody fragments include Fab, Fab', F(ab').sub2 and Fv fragments; diabodies; linear antibodies; single-chain antibody molecules; multispecific antibodies formed from antibody fragments.

The biologically active ingredient can also be a vaccine. Vaccines that can be incorporated in the hydrogels of the present invention include killed, but previously virulent, micro-organisms that have been treated with chemicals, heat, radioactivity or antibiotics. Examples include influenza, cholera, bubonic plague, polio, hepatitis A, and rabies. Further included are attenuated microorganisms, in particular attenuated viruses such as in the vaccines against viral diseases yellow fever, measles, rubella, mumps, and the bacterial disease typhoid. Further included is the *Mycobacterium tuberculosis* vaccine. A further type includes the toxoid-based vaccines such as tetanus and diphtheria vaccines. Still a further class of vaccines are those based on protein subunits (or protein fragments) such as the subunit vaccine against Hepatitis B virus, the virus-like particle (VLP) vaccine against human papillomavirus (HPV) and the *Haemophilus influenzae* type B vaccine.

The compositions of the invention can also be used for the controlled release of the various biologically active ingredients encapsulated in the hydrogel networks. Controlled release may be sustained delivery for periods varying from days (such as one day, two, three, four, five, six or seven days), to weeks (such as one week, two, three or four weeks) or even months (such as one month, or two or three months).

The compositions of the invention preferably contain the active ingredient in a therapeutically effective amount, which refers to an amount effective in the prevention or treatment of a disease or disorder, for the prevention or treatment of which the active ingredient is effective. The compositions may be used in a method of treatment of or prophylaxis in a patient suffering from a disease or disorder, said method comprising the administration to said patient a therapeutically effective amount of the composition.

The compositions of the invention can take the form of pharmaceutical compositions comprising a hydrogel as described herein and biologically active ingredient, in particular may be an active pharmaceutical ingredient. If desired the compositions may contain further carrier materials.

Preferred are compositions for parenteral use, in particular parenteral pharmaceutical compositions for subcutaneous or intramuscular administration. The parenteral pharmaceutical compositions may contain any of the carrier materials customarily used in such compositions. The compositions of the invention can also be formulated such that they are fit for implantation. In that instance the viscosity may be increased to obtain a more solid (in particular solid like) consistency.

The compositions can be prepared by adding the biological material to the hydrogels or, which is preferred, by adding the biological material to the hydrogel-forming mixture so that it becomes incorporated into the hydrogel network during its formation.

The biological materials can also be living matter such as cells, which are incorporated in the hydrogels of the invention. The latter form a scaffold in which the encapsulated cells maintain viability and function.

Such materials can be used in cell therapy or in tissue engineering applications, where hydrogel encapsulated cells are injected or implanted in the body in the desired site to affect therapy or respectively to regenerate damaged or diseased tissues.

Depending on the cell type, the hydrogel compositions of the present invention may be injected or implanted into any acceptable tissue such as, for example, cartilage, bone, tendon, ligament, intervertebral disc, meniscus, bladder, cardiac muscle, skeletal muscle, myocardium, fascia, adipose tissue, nerve, heart valve, intestine, lung, blood vessels, as well as organs such as kidney, liver, pancreas, stomach, and colon. In specific embodiments, the cells may be tenocytes, fibroblasts, ligament cells, endothelial cells, lung cells, epithelial cells, smooth muscle cells, cardiac muscle cells, skeletal muscle cells, islet cells, neuronal cells, hepatocytes, kidney cells, bladder cells, urothelial cells, chondrocytes, and bone-forming cells.

In some embodiments in which encapsulated cells are non-proliferating cells, the latter may be pancreatic islets, hepatic cells, neural cells, renal cortex cells, vascular endothelial cells, thyroid or parathyroid cells, adrenal cells, thymic cells, ovarian cells, or chondrocytes. Further, the cells may be stem cells, such as bone marrow-derived stem cells, embryonic stem cells, umbilical cord-derived stem cells, placenta-derived stem cells, and amniotic fluid-derived stem cells.

Sources of the cells may include fetal or adult organisms, particularly mammals, or established cell lines.

In a particular aspect, the present invention is directed to a method or process for manufacturing hydrogel networks comprising a hydrogel forming peptide as described herein having living cells encapsulated therein. The preferred method or process comprises the step of forming the hydrogel under conditions (such as pH, temperature) in which the cells are viable and dispersing the living cells therein.

The hydrogel-based compositions containing cells may also be useful in cell-based high-throughput screening and drug discovery.

The hydrogels and hydrogel-based compositions of the invention may also be dried to form xerogels, which may be reconstituted by addition of water.

The peptides of the invention form stable hydrogels. The peptides and the hydrogels derived therefrom show increased proteolytic resistance lacking the rapid in vivo degradation of similar α-peptide gelators. They offer increased stability as compared to similar α-peptides. This allows the provision of drug delivery systems with prolonged release profiles. The peptide hydrogels of the invention provide prolonged in vivo release of biologically active ingredients, in particular of drugs. In addition the increased enzymatic stability of drug loaded hydrogels may avoid burst effects and may prevent enzymatic degradation of drugs susceptible thereto. The peptides and the hydrogels of the invention may be used for the preparation of extended-release formulations, with days-to-weeks delivery of therapeutics. The peptides of the invention and the hydrogels derived therefrom are very interesting materials to serve as stable scaffolds for biological materials such as cells.

In addition, the biological stability, mechanical strength and release properties can be tuned by structural modifications in the amino acid sequence of the peptides. The peptides possess tunable storage moduli and form transparent self-supporting gels with shear-thinning behavior.

It was found that the use of higher gelation concentrations (i.e. the concentration required to obtain a self-supporting hydrogel) in comparison to the gelation concentration of similar self-assembling α-peptides (where typically a 0.5%-1% w/v concentration is used), such as a concentration of 2%-3% w/v, or higher, offer certain advantages. Under these circumstances the hydrogels of the invention form a more physically entangled network.

This results in more rigid hydrogels (which is an important property for biomaterials such as in cell therapy) and the dense network more efficiently encapsulates its cargo resulting in prolonged release profiles with a reduced number of burst effects.

The present invention is further illustrated in the following non-limiting examples.

EXAMPLES

Example 1: Synthesis and Purification of the Peptides

The peptides were prepared using standard 9-fluorenylmethoxycarbonyl (Fmoc) strategy. While the synthesis of mixed α/β-peptide H-FEβ$^3$hFFQβ$^3$hFFK-OH (SEQ ID NO. 1) was carried out on Fmoc-Lys(Boc)-loaded Wang resin (FluoroChem, 100-200 mesh, 0.35 mmol g-1), mixed α/β-peptides H-FEβ$^3$hFFQβ$^3$hFFK-NH$_2$ (SEQ ID NO. 2) and H-FEβ$^3$hFYQβ$^3$hFYK-NH$_2$ (SEQ ID NO. 3) were assembled on Fmoc-Rink Amide resin (Chem-Impex, 200-400 mesh, 0.60 mmol g-1). Nα-Fmoc-L-betaβ-homophenylalanine (2 equiv.) was pre-activated by HATU (2 equiv.) in DMF for 1 minute at room temperature and the α-amino acids (4 equiv.) were pre-activated by TBTU (4 equiv.). The peptides were cleaved manually from the solid support and the side chains were deprotected using a trifluoroacetic acid (TFA)/triisopropylsilane (TIS)/water (9.5:2.5:2.5, v/v/v) mixture at room temperature for 1.5 h. Subsequently, ~90% of the cleavage cocktail was evaporated. The crude peptides were precipitated in cold ether and washed three times by cold diethyl ether. Next, the crude peptides were dissolved in water and lyophilized before purification. Preparative reverse-phase high-performance liquid chromatography (HPLC) was used for the purification of all crude peptides. During the purification of the peptides, solvent A consisted of 0.1% TFA in water and solvent B was 0.1% TFA in acetonitrile. A linear gradient of 3 to 100% B in 20 min was applied. The purity of each peptide was verified by analytical reverse-phase liquid chromatography (RPLC) methods based on the same solvent system and gradient. The resulting pure peptides (>95%) were obtained after lyophilization of the collected fractions.

Reference peptide H-FEFQFK-OH (SEQ NO. 23) was prepared as described in J. Mater. Chem. B, 2015, 3, 759.

Example 2: Peptide Self-Assembly

Peptide self-assembly was analyzed in i) a PBS solution (10 mM), ii) a PBS/mQ mixture (1:1 v:v, mQ water with a resistivity of 18.2 mΩ·cm) or iii) a NaCl aqueous solution (150 mM). The TFA salt of reference peptide SEQ NO. 23 (1 mg) was dissolved in 50 µl mQ water, followed by the addition of 50 µl PBS solution. This mixture was left to rest overnight, resulting in a 1% w/v hydrogel. The TFA salt of mixed α/β-peptides SEQ ID NO 1 and SEQ ID NO 2 (2 mg) was dissolved in mQ (100 µL) and PBS/mQ mixture (100 µL), respectively. Gelation occurred almost instantaneously. The TFA salt of mixed α/β-peptide SEQ ID NO 3 (3 mg) was dissolved in PBS (100 µL) to probe gelation. All self-assembled gels were analyzed by circular dichroism (CD) and Fourier transform infrared (FT-IR) spectroscopy, as well as cryogenic transmission electron microscopy (Cryo-TEM).

Ft-Ir Analysis.

FT-IR spectra were collected on a Nicolet™ 6700 FT-IR spectrometer in attenuated total reflectance (ATR) mode using a diamond ATR sample holder. An aliquot of the gel was transferred on the diamond. Scans were performed between 4000 and 600 cm$^{-1}$ with 64 accumulations at a resolution of 0.4 cm$^{-1}$.

CD Spectroscopy Analysis.

The secondary structure of the peptides was analyzed using a 0.1 cm quartz cell on a Jasco™ J815 Spectropolarimeter, with 1 s integrations, 1 accumulation and a step size of 1 nm with a band width of 1 nm over a range of wavelengths from 200 to 270 nm. Peptide hydrogels were freshly prepared in their corresponding gelation conditions (see above peptide self-assembly) directly in the CD cell and spectra were recorded after 2 h. Measurements were repeated at least 3 times and their average was plotted.

Cryo-TEM Analysis.

A laboratory-built humidity-controlled vitrification system is used to prepare the hydrogels for imaging in a thin layer of vitrified ice using cryo-TEM. Humidity is kept close to 80% for all experiments, and ambient temperature is 22° C. 200 Mesh copper grids coated with perforated carbon film (Lacey carbon film: ProSci-Tech™, Qld, Australia) is used for all experiments. Grids are glow discharged in nitrogen for 5 sec immediately before use. The hydrogels are prepared as described above and analyzed after 24 h. Approximately 4 µL aliquots of sample are pipetted onto each grid prior to plunging. After 30 sec adsorption time the grid is blotted manually using Whatman™ 541 filter paper. The grid is then plunged into liquid ethane cooled by liquid nitrogen. Frozen grids are stored in liquid nitrogen until required. The samples are examined using a Gatan™ 626 cryoholder (Gatan, Pleasanton, Calif., USA) and Tecnai™ 12 Transmission Electron Microscope (FEI, Eindhoven, The Netherlands) at an operating voltage of 120 kV. At all times low dose procedures are followed, using an electron dose of 8-10 electrons $Å^2$ for all imaging. Images are recorded using a FEI Eagle™ 4 k×4 k CCD camera (FEI, Eindhoven, The Netherlands).

Negative Staining TEM Analysis.

Carbon-coated 300-mesh copper grids are glow-discharged in nitrogen to render the carbon film hydrophilic. Hydrogels are prepared as described above, diluted to allow handling, and a 4 µl aliquot of the sample is pipetted onto each grid. After 30 seconds adsorption time, the excess is drawn off using Whatman™ 541 filter paper, followed by staining with 2% aqueous potassium phosphotungstate at pH 7.2, for 10 s. Grids are air-dried until needed. The samples are examined using a Tecnai™ 12 Transmission Electron Microscope (FEI, Eindhoven, The Netherlands) at an operating voltage of 120 KV. Images are recorded using a Megaview III™ CCD camera and AnalySIS™ camera control software (Olympus.) Each grid is systematically examined and imaged to reflect a representative view of the sample.

Example 3: Enzymatic Degradation Study of Peptides in Non-Gelating Conditions

The following biodegradation experiments were performed in order to assess biostability of peptides of the invention toward elastase, a prominent enzyme present in the subcutaneous compartment.

The following buffer was used to assay the proteolytic stability of the peptides towards elastase: 10 mM PBS at pH 7.2. First, a stock solution of elastase (60 µM in 10 mM PBS) was prepared. Peptides SEQ ID NO 1, 2 and 3 and reference α-peptide SEQ ID NO 23 were subjected to the degradation study and prepared as a stock solution of 350 µM in mQ water (with a resistivity of 18.2 mΩ·cm). Enzymatic degradation was carried out by incubation of peptide (900 µL, 350 µM) with the enzyme (150 µL, 60 µM) at 37° C. for 7 days. To preclude any pH-dependent effects on the enzyme's activity, the pH value was kept at pH 6.9±0.5 in all degradation experiments.

The enzyme concentration was selected such that the reference α-peptide SEQ ID NO 23 was completely degraded in less than 1 hour. In case of the α-peptide SEQ ID NO 23, aliquots (70 µL) were periodically taken at 0 min, 5 min, 10 min, 15 min, 20 min and 30 min, while for the mixed α/β-peptides aliquots (70 µL) were taken at 0 min, 20 min, 30 min, 1 h, 2 h, 5 h, 1 day, 2 days, 3 days, 4 days, 5 days and 6 days. 5 µL of 25% AcOH in water (v/v) were added and the degradation was monitored by HPLC analysis. After just 30 min of exposure to elastase, the reference α-peptide SEQ ID NO 23 was completely degraded. The enzymatic degradation of mixed α/β-peptides SEQ ID NO 1, SEQ ID NO 2 and SEQ ID NO 3 was remarkably slower and lasted several days. Mixed α/β-peptides SEQ ID NO 1 and SEQ ID NO 2 were completely consumed after 6 days whilst mixed α/β-peptide SEQ ID NO 1, SEQ ID NO 3 was degraded after 3 days.

Example 4: Enzymatic and Erosion Degradation Study of Hydrogels (A). The peptide hydrogel (1 mL) was prepared in a 10 mL glass tube using the appropriate gelation conditions (see peptide self-assembly in example 2). After leaving the hydrogel to rest overnight the degradation evaluation was started. First, general stability (without the incubation of an enzyme) was evaluated for α-peptide SEQ ID NO 23: 3 mL of mQ water was gently placed on top of the hydrogel and erosion experiments were performed by placing 3 mL PBS solution (10 mM) on top of the hydrogel to assess the hydrogels macroscopic decay in time. A small opaque band rapidly appeared at the hydrogel-PBS interface and after 2 hours, upon inversion of the tube and collection of the liquid fraction (3 mL) in a separate vial, a hydrogel of 1 mL was observed with small visual traces of aggregation at its surface. After 24 hours there was a small loss in volume (0.1 mL) of the formed hydrogel and the aggregation remained visible at the hydrogel surface. The PBS fraction was recollected and measured as 3.1 mL, in agreement with the 0.1 mL volume loss of the hydrogel. After 4 days the hydrogel was completely disintegrated into opaque aggregated pieces sticking to the bottom of the glass tube. The collected solution was measured to be 3.8 mL.

(B) The proteolytic stability of the hydrogels was analyzed by placing an elastase solution (60 µM in 10 mM PBS) on top of the hydrogel. In all the stability experiments a total volume of 4 mL (gel+PBS solution with and without enzyme) was obtained. The addition of the enzyme solution on top of the hydrogel was set as the starting point of the gel-degradation experiments; B. At specific time-intervals (0 h, 24 h, 2 days, 3 days, 4 days, 5 days, 6 days, 7 days, 2 weeks, 3 weeks, etc.) the liquid portion on top of the hydrogel was removed using a pipette and the hydrogel's volume was estimated using following formula:

$$V_{Total} - V_{Liquid\ portion} = V_{Hydrogel} \quad (1)$$

wherein $V_{Total}$ is the total volume and remains at 4 mL and $V_{Liquid\ portion}$ is the volume measured of the liquid portion after each sampling interval. At each sampling interval the pH was also measured; C. A picture of the inverted glass tube, only containing the self-sustaining non-fluid-like hydrogel, was taken in order to assess the physical deformation of the hydrogel and volume-loss; D. The PBS, mQ or enzyme solution is gently replaced on top of the hydrogel using a pipette, allowing repetition of steps A-D. Between sampling-intervals the glass tubes were kept undisturbed at room temperature. The gel degradation time was defined as the period required for complete disintegration of the hydrogels into liquid under observation of the naked eye.

After 2 days the internal structure of the hydrogel of α-peptide SEQ ID NO 23 started to change into an opaque structure. The hydrogel became unstable/fluid-like after 3.5 days.

(C) In a next step, the stability and degradation profiles of the mixed α/β-hydrogels were investigated using this methodology. During the first hours after addition of the elastase to peptide SEQ ID NO 1 hydrogel, no apparent physical deformation was observed. The collected liquid portion (on top of the hydrogel) measured 3 mL (during the first 10 hours). HPLC showed the chemical degradation of the hydrogel through elastase activity. In comparison to the α-peptide 1 hydrogel the degradation time of peptide SEQ ID NO 1 hydrogel was extended from 3.5 days to 5.5 days. However, the physical alteration of this hydrogel into an opaque structure was already observed after one day.

Peptide SEQ ID NO 2 hydrogel showed a different biodegradation resistance profile towards elastase, as compared to mixed α/β-peptide SEQ ID NO 1 hydrogel. No aggregation was observed (white opaque structures). Aggregation can negatively influence undesired release of entrapped cargoes with e.g. burst effects or incomplete releases. During the biodegradation experiment (which ran for over 42 days) no macroscopic aggregation was observed. Nonetheless, HPLC analysis confirmed the enzymatic degradation of peptide SEQ ID NO 2 hydrogel, similar to the previous biodegradation experiments. This hydrogel appeared to be remarkably stable during the biodegradation experiment: after 35 days the hydrogel's volume was only reduced to approximately half of its original volume and remained self-supporting.

Peptide SEQ ID NO 3 hydrogel was found to be even more stable and showed no significant physical degradation nor aggregation for over 42 days, albeit it did show some chemical degradation (confirmed by HPLC analysis). This hydrogel showed remarkable physical stability (no observable volume loss for over 42 days).

Example 5: Drug Release

The cargo material is added as a solution to the hydrogel based on peptide with SEQ 1 (H-FEβ$^3$hFFQβ$^3$hFFK-OH) prepared as described above. The resulting hydrogel concentration is 2% w/v with 0.1% w/v ciprofloxacin cargo.

2 mg of the peptide with SEQ 1 trifluoroacetate salt is centrifuged in an Eppendorf apparatus so that all the peptide salt is at the bottom of the Eppendorf) and 100 µL of a 0.1% w/v ciprofloxacin solution in mQ water are added (0.1 mg/100 µL mQ water). If the resulting system is not clear (aggregates inside), the mixture is heated up (heat gun) and sonicate or by using a ThermoMixer™ apparatus at 900 rpm for 3½ min at 65° C. Upon obtaining a clear hydrogel, it is allowed to set for a couple of seconds. Once the hydrogel is set, 0.5 mL phosphate buffered saline (PBS) is added on top of the hydrogel, after which the release experiment is started.

At regular time intervals 254 samples are taken from the PBS on top of the hydrogel, 25 µL mQ water is added to produce a 504 sample for HPLC analysis. 25 µL of PBS is then added to the solution on top of the hydrogel.

Full Release Analysis:

a cargo sample is prepared in PBS having the same amount of cargo material as encapsulated in the hydrogel. The sample analysis protocol is used for HPLC analysis.

The full release of a 0.1% w/v encapsulated ciprofloxacin solution is calculated as follows: a solution corresponding to 0.1 mg in 0.5 mL PBS (maximum amount of cargo to be found in the 0.5 mL PBS placed on top) is prepared. From this solution a 25 µL sample is taken and 25 µL mQ water are added to prepare the HPLC sample (which is identical to sample analysis).

HPLC analysis: 2 µL injection, 215 or 254 nm.

Calculation: area under peak is determined using HPLC software (corresponding to the entrapped cargo) for the released fraction:

((Area under cargo peak)/(Area under peak calculated for full release))*100%=estimated release (%)

For peptide-cargos the amount injected in the HPLC is 10 µL (because of the low absorption of some peptide cargos). This is also taken into account when calculating the full release of these peptide cargos.

Example 6: Alternative Methods for the Synthesis and Purification of Peptides

The peptides were prepared using standard 9-fluorenylmethoxycarbonyl (Fmoc) strategy. All syntheses were carried out on Fmoc-Rink Amide resin (ChemImpex, 100-200 mesh, 0.47 mmol g$^{-1}$).

H-FEβ$^3$hFFQFQβ$^3$hFFK-NH$_2$ (SEQ ID NO: 22) and H-Fβ$^2$hFEFQFK-NH2 (SEQ ID NO:19) were prepared as follows: Nα-Fmoc-L-β$^3$-homophenylalanine (3 equiv.) and α-amino acids (3 equiv.) were pre-activated by HBTU (3 equiv.) and DIPEA (4 equiv.) in DMF for 1 minute at room temperature. Nα-Fmoc-L-β$^2$-homophenylalanine (2 equiv.) was pre-activated by HBTU (2 equiv.) and DIPEA (3 equiv.) in DMF. Coupling reactions were carried out at room temperature for 40 minutes in case of α-amino acids, for 1 hour for Nα-Fmoc-L-β$^3$-homophenylalanine and for 6 hours for Nα-Fmoc-L-β$^2$-homophenylalanine. Fmoc-deprotection was executed in two steps (5 minutes+15 minutes) with a solution of 4-methylpiperidine in DMF (20 v/v %) at room temperature. Washing steps were performed with DMF (3×1 minute) and DCM (3×1 minute).

The peptide was cleaved manually from the solid support and the side chains were deprotected using a trifluoroacetic acid (TFA)/triisopropylsilane (TIS)/water (9.5:2.5:2.5, v/v/v) mixture at room temperature (2×1.5 h). Subsequently, the cleavage cocktail was evaporated under vacuum and the crude peptides were precipitated in diethyl ether. The precipitate was dissolved in a mixture of water and acetonitrile, and lyophilized.

Purification was carried out by preparative reverse-phase high-performance liquid chromatography (RP-HPLC). Solvent A consisted of 0.1% TFA in water and solvent B of 0.1% TFA in acetonitrile. A linear gradient of 10 to 70% in 30 min was used.

The purity of all peptides was verified by analytical reverse-phase liquid chromatography, using the same solvent system as previously stated with a gradient of 3 to 97% B in 20 min. The resulting pure peptides (>98%) were obtained after lyophilisation of the collected fractions.

Gelation Conditions for β$^3$-homophenylalanine Sequences:

For H-FEβ$^3$hFFQFQβ$^3$hFFK-NH$_2$ (SEQ ID NO:22 (=10-mer)), 100 µl mQ water was added to 2 mg of TFA-salt of pure peptide, then vortexed and sonicated. As a result, a transparent self-supporting gel was formed immediately. A gelation condition of 2 w/v % in mQ water was found.

Gelation Conditions for β$^2$-homophenylalanine Sequences:

for H-Fβ$^2$hFEFQFK-NH$_2$ (SEQ ID NO:19), 100 µl of PBS was added to 2 mg of TFA-salt of pure peptide, then vortexed and sonicated. After overnight resting, a self-supporting gel was formed. A gelation condition of 2 w/v % in PBS was determined.

The invention claimed is:

1. A hydrogel-forming peptide comprising from 5 to 12 amino acid residues, wherein the amino acid residues are selected from hydrophobic and hydrophilic amino acid residues;

wherein the hydrophobic amino acid residues are independently selected from alanine, valine, leucine, isoleucine, phenylalanine, tyrosine, tryptophan and cyclohexylalanine;

wherein the hydrophilic amino acid residues are independently selected from asparagine, glutamine, arginine, histidine, lysine, ornithine, aspartic acid and glutamic acid;

wherein the peptide further comprises one, two, or three dyads of hydrophobic amino acid residues, wherein at least one dyad contains a β-homo amino acid residue;

wherein each dyad is separated from any other dyad or hydrophobic amino acid residue by a hydrophilic amino acid residue;

wherein the amino acid residues that are not a β-homo amino acid residue are α-amino acid residues;

wherein the N-terminus of the hydrogel-forming peptide:

bears two $R^a$ groups each independently selected from $R^1$, or bears one $R^1$ group and one group selected from $C(=Z)R^1$, $C(=Z)ZR^1$, $C(=Z)NHR^1$ and $C(=Z)N(R^1)_2$;

wherein each Z independently is O or S; and each $R^1$ is independently selected from H, optionally substituted linear or branched $C_{1-10}$alkyl, optionally substituted $C_{3-10}$cycloalkyl, optionally substituted aryl$C_{1-6}$alkyl and optionally substituted aryl;

wherein the C-terminus of the hydrogen forming peptide forms a group $C(=O)OR^2$ or $C(=O)N(R^2)_2$; and wherein each $R^2$ independently is selected from H, optionally substituted linear or branched $C_{1-10}$alkyl, optionally substituted $C_{3-10}$cycloalkyl, optionally substituted aryl$C_{1-6}$alkyl, and optionally substituted aryl;

or a salt form thereof.

2. The hydrogel-forming peptide of claim 1, wherein the peptide has the following general formula I:

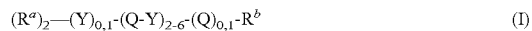

$$(R^a)_2-(Y)_{0,1}-(Q-Y)_{2-6}-(Q)_{0,1}-R^b \quad \quad (I)$$

wherein each Q independently is a hydrophobic amino acid residue or a dyad of hydrophobic amino acid residues; wherein one, two or three of said Q is a dyad of a hydrophobic α-amino acid residue and a β-homo amino acid residue;

each Y independently is a hydrophilic α-amino acid residue;

the group $(Y)_{0,1}$ represents a bond or a hydrophilic α-amino acid residue Y;

the group $(Q)_{0,1}$ represents a bond or a group Q;

$(R^a)_2$ represents two $R^a$ groups, substituted on the terminal nitrogen of said peptide, the IV groups are each independently selected from $R^1$, or $R^a$ groups represent one $R^1$ group and one group selected from $C(=Z)R^1$, $C(=Z)ZR^1$, $C(=Z)NH(R^1)$ and $C(=Z)N(R^1)_2$;

wherein each Z independently is O or S; and each $R^1$ is independently selected from H, optionally substituted linear or branched $C_{1-10}$alkyl, optionally substituted $C_{3-10}$ cycloalkyl, optionally substituted aryl$C_{1-6}$alkyl, and optionally substituted aryl;

$R^b$ is a group $OR^2$ or $N(R^2)_2$;

wherein each $R^2$ independently is selected from H, optionally substituted linear or branched $C_{1-10}$alkyl, optionally substituted $C_{3-10}$cycloalkyl, optionally substituted aryl$C_{1-6}$alkyl, and optionally substituted aryl;

wherein the peptide has from 5 to 12 amino acid residues; or a salt form thereof.

3. The hydrogel-forming peptide of claim 2, wherein $—(Y)_{0,1}—$ is a bond;

the first Q-Y group represents a group —X—Y—, wherein X is Phe, Tyr, or Trp; Y is Glu, Gln, Asp or Asn;

two, three, or four -(Q-Y)— groups are present, wherein one, two or three Q groups are dyads; wherein each dyad independently is of formula -β³homo-Phe-Phe-, or -β³homo-Phe-Tyr-; each Y independently is Lys, Glu, Gln, Asp or Asn; and $-(Q)_{0,1}-$ is a bond.

4. The hydrogel-forming peptide of claim 1, wherein within dyads comprising a $β^3$-homo amino acid residue, the $β^3$-homo amino acid residue is positioned closest to the N-terminus; and wherein within dyads comprising a $β^2$-homo amino acid residue, the $β^2$-homo amino acid residue is positioned closest to the C-terminus.

5. The hydrogel-forming peptide of claim 1, wherein at least one hydrophilic amino acid residue has a side chain that is positively charged at physiological pH and at least one hydrophilic amino acid residue has a side chain that is negatively charged at physiological pH.

6. The hydrogel-forming peptide of claim 1, wherein each hydrophobic amino acid residue independently is selected from phenylalanine, tyrosine, tryptophan and cyclohexylalanine; and each hydrophilic amino acid residue independently is selected from asparagine, glutamine, arginine, lysine, aspartic acid and glutamic acid.

7. The hydrogel-forming peptide of claim 1, wherein each β-homo amino acid residue is a β3-homo amino acid residue.

8. The hydrogel-forming peptide of claim 7, wherein each β3-homo amino acid is β3-homo phenylalanine or β3-homo tyrosine.

9. The hydrogel-forming peptide of claim 1, wherein the peptide is of formula (SEQ ID NO. 1)
H₂N-FEβ³hFFQβ³hFFK-OH (H₂N-Phe-Glu-β³hPhe-Phe-Gln-β³hPhe-Phe-Lys-OH), (SEQ ID NO. 2)
H₂N-FEβ³hFFQβ³hFFK-NH₂, (H₂N-Phe-Glu-β³hPhe-Phe-Gln-β³hPhe-Phe-Lys-NH₂), (SEQ ID NO. 3)
H₂N-FEβ³hFYQβ³hFYK-NH₂, (H₂N-Phe-Glu-β³hPhe-Tyr-Gln-β³hPhe-Tyr-Lys-NH₂), (SEQ ID NO. 4)
H₂N-FEβ³hFYQβ³hFYK-OH, (H₂N-Phe-Glu-β³Phe-Tyr-Gln-β³hPhe-Tyr-Lys-OH), (SEQ ID NO. 5)
H₂N-FQβ³hFFQβ³hFFK-OH (H₂N-Phe-Gln-β³hPhe-Phe-Gln-β³hPhe-Phe-Lys-OH), (SEQ ID NO. 6)
H₂N-FEβ³hFFK-NH₂, (H₂N-Phe-Glu-β³hPhe-Phe-Lys-NH₂), (SEQ ID NO. 7)
H₂N-FEβ³hFFK-OH, (H₂N-Phe-Glu-β³hPhe-Phe-Lys-OH), (SEQ ID NO. 9)
H₂N-FQβ³hFFK-NH₂ (H₂N-Phe-Gln-β³hPhe-Phe-Lys-NH₂), (SEQ ID NO. 10)
H₂N-β³hFFEβ³hFFK-NH₂, (H₂N-β³hPhe-Phe-Glu-β³hPhe-Phe-Lys-NH₂).

10. A hydrogel comprising the hydrogel-forming peptide of claim 1.

11. A composition comprising the hydrogel of claim 10 and one or more biological materials or one or more biologically active ingredients, or a combination thereof.

12. The composition of claim 11, wherein the biological material is a cell and/or the biologically active ingredient is an active pharmaceutical ingredient.

13. A process for preparing the hydrogel of claim 10 the process comprising:

dissolving the hydrogel-forming peptide in an aqueous medium containing a buffer, and allowing the formation of the hydrogel to take place.

14. The hydrogel-forming peptide of claim 1, wherein the hydrogel-forming peptide is a self-assembling hydrogel-forming peptide.

15. The hydrogel-forming peptide of claim 1, wherein the peptide is of formula:

(SEQ ID NO. 8)
H₂N-FEβ³hChaFQβ³hChaFK-OH, (H₂N-Phe-Glu-β³hCha-Phe-Gln-β³hCha-Phe-Lys-OH), (SEQ ID NO. 11)
H₂N-FEβ³hFFKF-NH₂ (H₂N-Phe-Glu-β³hPhe-Phe-Lys-Phe-NH₂), (SEQ ID NO. 12)
H₂N-Eβ³hFFKβ³hFF-NH₂ (H₂N-Glu-β³hPhe-Phe-Lys-β³hPhe-Phe-NH₂), (SEQ ID NO. 13)
H₂N-FEβ³hFFQFK-NH₂ (H₂N-Phe-Glu-β³hPhe-Phe-Gln-Phe-Lys-NH₂), (SEQ ID NO. 14)
H₂N-WEβ³hWWQWK-NH₂ (H₂N-Trp-Glu-β³hTrp-Trp-Gln-Trp-Lys-NH₂), (SEQ ID NO. 15)
H₂N-WEβ³hFFQWK-NH₂ (H₂N-Trp-Glu-β³hPhe-Phe-Gln-Trp-Lys-NH₂), (SEQ ID NO. 16)
H₂N-FEβ³hFFKβ³hFF-NH₂ (H₂N-Phe-Glu-β³hPhe-Phe-Lys-β³hPhe-Phe-NH₂), (SEQ ID NO. 17)
H₂N-β³hFFEFQFK-NH₂ (H₂N-β³hPhe-Phe-Glu-Phe-Gln-Phe-Lys-NH₂), (SEQ ID NO. 18)
H₂N-FEFQβ³hFFK-NH₂ (H₂N-Phe-Glu-Phe-Gln-β³hPhe-Phe-Lys-NH₂), (SEQ ID NO. 19)
H₂N-Fβ³hFEFQFK-NH₂ (H₂N-Phe-β³hPhe-Glu-Phe-Gln-Phe-Lys-NH₂), (SEQ ID NO. 20)
H₂N-FEβ³hFFQFKF-NH₂ (H₂N-Phe-Glu-β³hPhe-Phe-Gln-Phe-Lys-Phe-NH₂),

-continued (SEQ ID NO. 21)
H$_2$N-FEFQFKβ$^3$hFF-NH$_2$ (H$_2$N-Phe-Glu-Phe-Gln-Phe-Lys-β$^3$hPhe-Phe-NH$_2$), (SEQ ID NO. 22)
H$_2$N-FEβ$^3$hFFQFQβ$^3$hFFK-NH$_2$ (H$_2$N-Phe-Glu-β$^3$hPhe-Phe-Gln-Phe-Gln-β$^3$hPhe-Phe-Lys-NH$_2$).

\* \* \* \* \*

SEQUENCE LISTING

<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (8)..(8)
<223> OTHER INFORMATION: OH substituted

<400> SEQUENCE: 1

Phe Glu Phe Phe Gln Phe Phe Lys
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (8)..(8)
<223> OTHER INFORMATION: NH2 substituted

<400> SEQUENCE: 2

Phe Glu Phe Phe Gln Phe Phe Lys
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe -continued

```
<220> FEATURE:
<221> NAME/KEY: MISC_FEATURE
<222> LOCATION: (8)..(8)
<223> OTHER INFORMATION: NH2 substituted

<400> SEQUENCE: 3

Phe Glu Phe Tyr Gln Phe Tyr Lys
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (8)..(8)
<223> OTHER INFORMATION: OH substituted

<400> SEQUENCE: 4

Phe Glu Phe Tyr Gln Phe Tyr Lys
1               5

<210> SEQ ID NO 5
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (8)..(8)
<223> OTHER INFORMATION: OH substituted

<400> SEQUENCE: 5

Phe Gln Phe Phe Gln Phe Phe Lys
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
```

-continued

```
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (5)..(5)
<223> OTHER INFORMATION: NH2 substituted

<400> SEQUENCE: 6

Phe Glu Phe Phe Lys
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (5)..(5)
<223> OTHER INFORMATION: OH substituted

<400> SEQUENCE: 7

Phe Glu Phe Phe Lys
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: Beta-3-homocyclohexylalanine
<220> FEATURE:
<221> NAME/KEY: MISC_FEATURE
<222> LOCATION: (6)..(6)
<223> OTHER INFORMATION: Beta-3-homocyclohexylalanine
<220> FEATURE:
<221> NAME/KEY: MISC_FEATURE
<222> LOCATION: (8)..(8)
<223> OTHER INFORMATION: OH substituted

<400> SEQUENCE: 8

Phe Glu Xaa Phe Gln Xaa Phe Lys
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
```

```
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (5)..(5)
<223> OTHER INFORMATION: NH2 substituted

<400> SEQUENCE: 9

Phe Gln Phe Phe Lys
1               5

<210> SEQ ID NO 10
<211> LENGTH: 6
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (1)..(1)
<223> OTHER INFORMATION: beta-3-homoPhe
<220> FEATURE:
<221> NAME/KEY: MISC_FEATURE
<222> LOCATION: (4)..(4)
<223> OTHER INFORMATION: beta-3-homoPhe
<220> FEATURE:
<221> NAME/KEY: MISC_FEATURE
<222> LOCATION: (6)..(6)
<223> OTHER INFORMATION: NH2 substituted

<400> SEQUENCE: 10

Phe Phe Glu Phe Phe Lys
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: NH2 substituted

<400> SEQUENCE: 11

Phe Glu Phe Phe Lys Phe
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
```

```
<220> FEATURE:
<221> NAME/KEY: MISC_FEATURE
<222> LOCATION: (2)..(2)
<223> OTHER INFORMATION: beta-3-homoPhe
<220> FEATURE:
<221> NAME/KEY: MISC_FEATURE
<222> LOCATION: (5)..(5)
<223> OTHER INFORMATION: beta-3-homoPhe
<220> FEATURE:
<221> NAME/KEY: MISC_FEATURE
<222> LOCATION: (6)..(6)
<223> OTHER INFORMATION: NH2 substituted

<400> SEQUENCE: 12

Glu Phe Phe Lys Phe Phe
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 13

Phe Glu Phe Phe Gln Phe Lys
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: Beta-3-homoTrp
<220> FEATURE:
<221> NAME/KEY: MISC_FEATURE
<222> LOCATION: (7)..(7)
<223> OTHER INFORMATION: NH2 substituted

<400> SEQUENCE: 14

Trp Glu Trp Trp Gln Trp Lys
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
```

```
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 15

Trp Glu Phe Phe Gln Trp Lys
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (6)..(6)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 16

Phe Glu Phe Phe Lys Phe Phe
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (1)..(1)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 17

Phe Phe Glu Phe Gln Phe Lys
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
```

```
<220> FEATURE:
<221> NAME/KEY: MISC_FEATURE
<222> LOCATION: (5)..(5)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 18

Phe Glu Phe Gln Phe Phe Lys
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (2)..(2)
<223> OTHER INFORMATION: beta-3-homoPhe
<220> FEATURE:
<221> NAME/KEY: MISC_FEATURE
<222> LOCATION: (7)..(7)
<223> OTHER INFORMATION: NH2 substituted

<400> SEQUENCE: 19

Phe Phe Glu Phe Gln Phe Lys
1               5

<210> SEQ ID NO 20
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (8)..(8)
<223> OTHER INFORMATION: NH2 substituted

<400> SEQUENCE: 20

Phe Glu Phe Phe Gln Phe Lys Phe
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (7)..(7)
<223> OTHER INFORMATION: beta-3-homoPhe
```

```
<220> FEATURE:
<221> NAME/KEY: MISC_FEATURE
<222> LOCATION: (8)..(8)
<223> OTHER INFORMATION: NH2 substituted

<400> SEQUENCE: 21

Phe Glu Phe Gln Phe Lys Phe Phe
1               5

<210> SEQ ID NO 22
<211> LENGTH: 10
<212> TYPE: PRT
<213> ORGANISM: Artificial Sequence
<220> FEATURE:
<223> OTHER INFORMATION: synthetic beta-peptides
<220> FEATURE:
<221> NAME/KEY: MISC_FEATURE
<222> LOCATION: (1)..(1)
<223> OTHER INFORMATION: hydrogen substituted
<220> FEATURE:
<221> NAME/KEY: MISC_FEATURE
<222> LOCATION: (3)..(3)
<223> OTHER INFORMATION: beta-3-homoPhe
<220> FEATURE:
<221> NAME/KEY: MISC_FEATURE
<222> LOCATION: (8)..(8)
<223> OTHER INFORMATION: beta-3-homoPhe
<220> FEATURE:
<221> NAME/KEY: MISC_FEATURE
<222> LOCATION: (10)..(10)
<223> OTHER INFORMATION: NH2 substituted

<400> SEQUENCE: 22

Phe Glu Phe Phe Gln Phe Gln Phe Phe Lys
1               5                   10
```